United States Patent
Lee et al.

(10) Patent No.: US 8,216,288 B2
(45) Date of Patent: Jul. 10, 2012

(54) PIN SITE WOUND PROTECTION SYSTEM

(76) Inventors: Harry Lee, Birmingham, AL (US);
Joshua Reardon, Tuscaloosa, AL (US);
Dror Paley, Owings Mills, MD (US)

( * ) Notice: Subject to any disclaimer, the term of this patent is extended or adjusted under 35 U.S.C. 154(b) by 761 days.

(21) Appl. No.: 11/995,757

(22) PCT Filed: Jul. 19, 2006

(86) PCT No.: PCT/US2006/028004
§ 371 (c)(1),
(2), (4) Date: Aug. 12, 2008

(87) PCT Pub. No.: WO2007/013912
PCT Pub. Date: Feb. 1, 2007

(65) Prior Publication Data
US 2009/0149891 A1 Jun. 11, 2009

Related U.S. Application Data
(60) Provisional application No. 60/701,346, filed on Jul. 21, 2005.

(51) Int. Cl.
*A61B 17/04* (2006.01)
*A61B 17/84* (2006.01)
(52) U.S. Cl. ........................... 606/322; 606/329
(58) Field of Classification Search ............... 606/53–59, 606/322–324, 329, 96–97, 104–105; 604/174, 604/178, 180; 602/1–79; 24/4, 30.5 W, 72.5, 24/545–552, 563
See application file for complete search history.

(56) References Cited

U.S. PATENT DOCUMENTS
| | | | | |
|---|---|---|---|---|
| 2,583,020 A | * | 1/1952 | Smith | 24/551 |
| 3,140,519 A | * | 7/1964 | Johnson | 24/30.5 R |
| 4,005,709 A | | 2/1977 | Laerdal | |
| 4,556,060 A | | 12/1985 | Perlin | |
| 4,747,407 A | | 5/1988 | Liu et al. | |
| 4,943,293 A | * | 7/1990 | Lee, Jr. | 606/96 |
| 5,360,020 A | * | 11/1994 | Lee et al. | 128/888 |
| 5,702,388 A | | 12/1997 | Jackson et al. | |
| 7,723,559 B2 | * | 5/2010 | Linnane et al. | 602/42 |
| 2002/0151859 A1 | * | 10/2002 | Schoelling | 604/385.17 |

* cited by examiner

*Primary Examiner* — Thomas Barrett
*Assistant Examiner* — Matthew Lawson
(74) *Attorney, Agent, or Firm* — Kenneth M. Bush; Bush Intellectual Property Law

(57) ABSTRACT

An improved disposable pin site wound protection system for covering the entry or exit site of a surgical pin, wherein the system substantially reduces the time required to change a dressing at a pin site wound. The invention comprises a sponge (11) and clip (21), both of which are designed to be attached to a pin (15) adjacent a wound. The clip (21), when compressed, crosses the legs (23, 25) of the clip and when released will attach to the full-range of external fixation pins and wires. This reverse action of the clip, opening when compressed and closing when released, is a self-closing and self-holding clip that can be applied and removed with one hand. The sponge (11) is preferably cylindrical or hemispherical in shape, and may include a spiral cut (12) to resist accidental displacement from the pin.

7 Claims, 5 Drawing Sheets

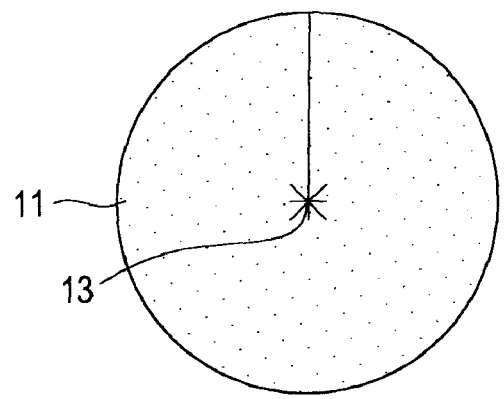
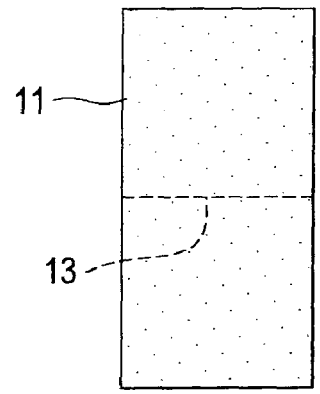
FIG. 9A  FIG. 9B
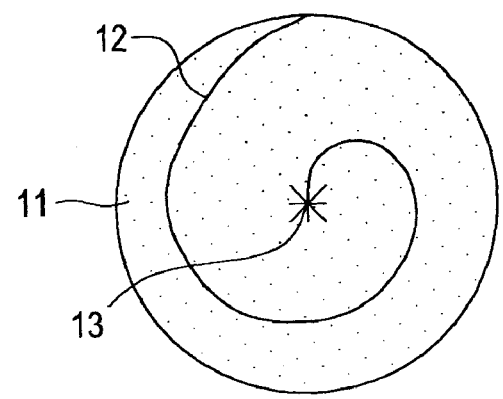
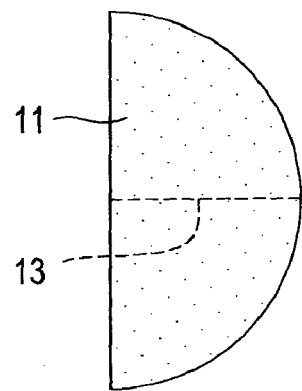
FIG. 10A  FIG. 10B

PIN SITE WOUND PROTECTION SYSTEM

This application claims priority to U.S. Provisional Patent Application No. 60/701,346, filed Jul. 21, 2005, the disclosure of which is incorporated herein by reference.

TECHNICAL FIELD

The present invention relates to medical devices, and more particularly, to a surgical dressing for covering the entry or exit site of a surgical pin or surgical wire.

BACKGROUND ART

Fixation of severely broken bones frequently requires the use of a plurality of surgical pins, wires, or similar implements inserted radially into the injured limb, with the distal ends protruding outwardly through a patient's skin. Such surgical implements, referred to collectively herein as pins, may be integral components of complex fixation systems, and may remain in position for several days, weeks, or even months, depending upon the severity of the injury and other factors. Examples of prior art pin site wound protection systems are described in U.S. Pat. Nos. 4,943,293 and 5,360,020, the disclosures of which are incorporated herein by reference.

In order to minimize the risk of infection, it is essential that the wound dressings be regularly changed. Unfortunately, prior art pin site wound protection systems do not allow convenient changing of the wound dressings and are not designed for single-handed application by poly-trauma patients. Further, the appearance of the wound where the surgical pin enters or exits the skin is unsightly, causing psychological trauma in some patients, especially children. As a result of the substantial time required to change such a wound dressing, together with the unappealing appearance of the wound, patient compliance with the prescribed schedule for changing the wound dressing is reduced.

The present invention seeks to overcome the foregoing deficiencies by providing an inexpensive pin site wound protection system designed for single-handed manipulation and to allow rapid changing of wound dressings.

SUMMARY OF THE INVENTION

The present invention is an improved disposable pin site wound protection system for covering the entry or exit site of a surgical pin such as a halo pin, external fixation pin, traction pin, or surgical wire, wherein the system substantially reduces the time required to change a dressing at a pin site wound. The invention comprises a sponge and clip, both of which are designed to be attached to a pin adjacent a wound. The clip, when compressed, crosses the legs of the clip and when released will attach to the full-range of external fixation pins and wires. This reverse action of the clip, opening when compressed and closing when released, is a self-closing and self-holding clip that can be applied and removed with one hand. Unlike existing devices, the clip allows pressure against the sponge for immediate post-operative cessation of bleeding at the pin site and can be backed off to vary the pressure according to the stage of healing. The sponge is preferably cylindrical or hemispherical in shape, and may include a spiral cut to resist accidental displacement from the pin. The sponge may be of various medical grade materials and may or may not be impregnated with antiseptic or other anti-pathogenic agents.

BRIEF DESCRIPTION OF THE DRAWINGS

FIG. 9A is a front elevational view of a cylindrical sponge.

FIG. 9B is a side view of a cylindrical sponge.

FIG. 10A is a front elevational view of a hemispherical sponge.

FIG. 10B is a side view of a hemispherical sponge.

BEST MODES FOR CARRYING OUT THE INVENTION

Figure 1:
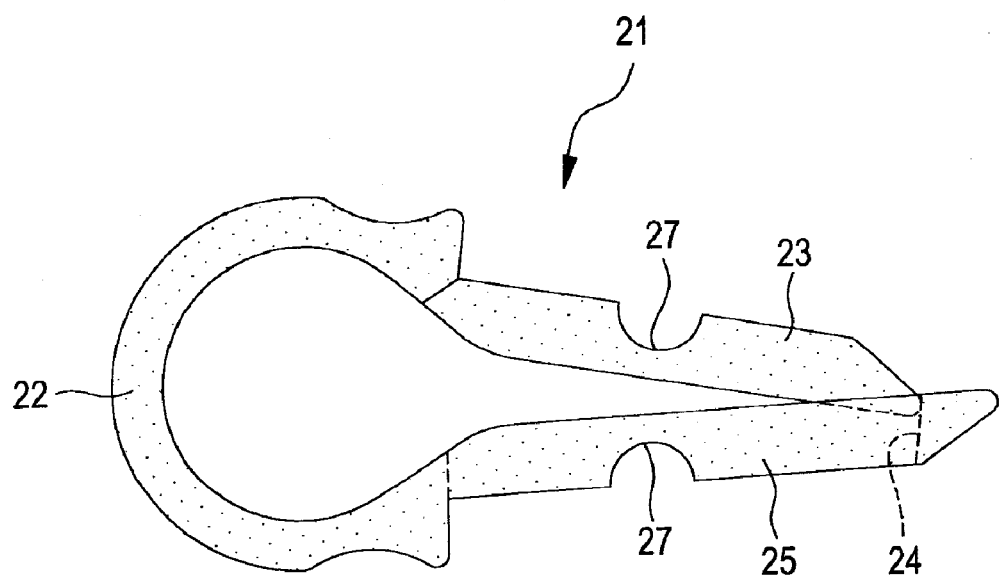
FIG. 1 is a right side elevational view of the clip of the present invention.

The present invention comprises a sponge 11 and a clip 21, both of which are designed to be attached to a pin 15 adjacent a wound. The sponge 11 may have any prior art design, such as a cylindrical design (FIGS. 9A-9B), or the sponge 11 may be hemispherical (FIGS. 10A-10B). A hemispherical sponge allows pressure to be applied to the pin exit site by the spherical side of the sponge or, alternatively, the sponge could be turned around so the flat side would disperse pressure over a wider area. The sponge 11 may include a spiral cut 12, shown in the hemispherical sponge in FIGS. 10A-10B, to resist accidental displacement from the pin 15. To secure a spiral cut sponge, the sponge is twisted onto the pin 15 until the pin 15 is within the central axial opening 13 through the sponge. The spiral cut may be in other shaped sponges as well.

Figure 2:
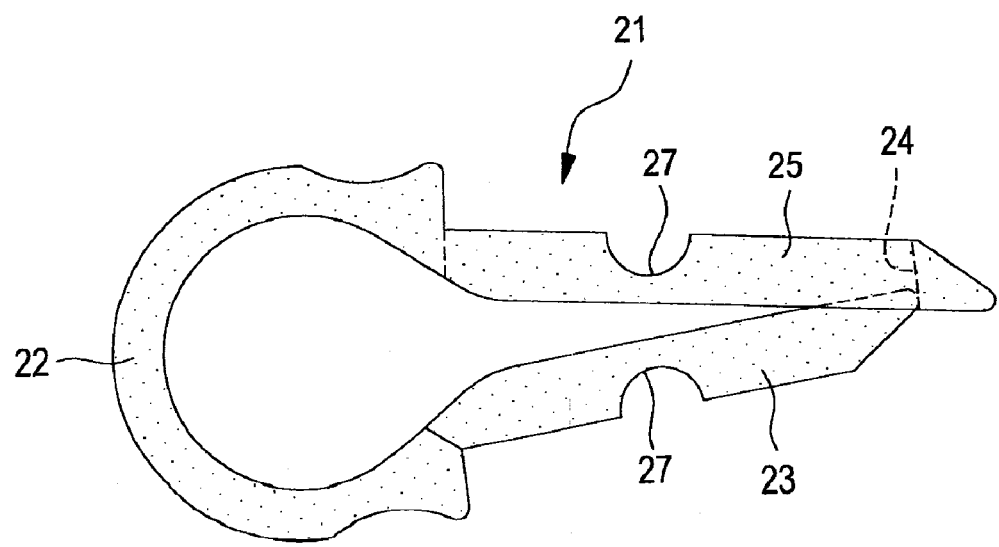
FIG. 2 is a left side elevational view of the clip.
Figure 3:
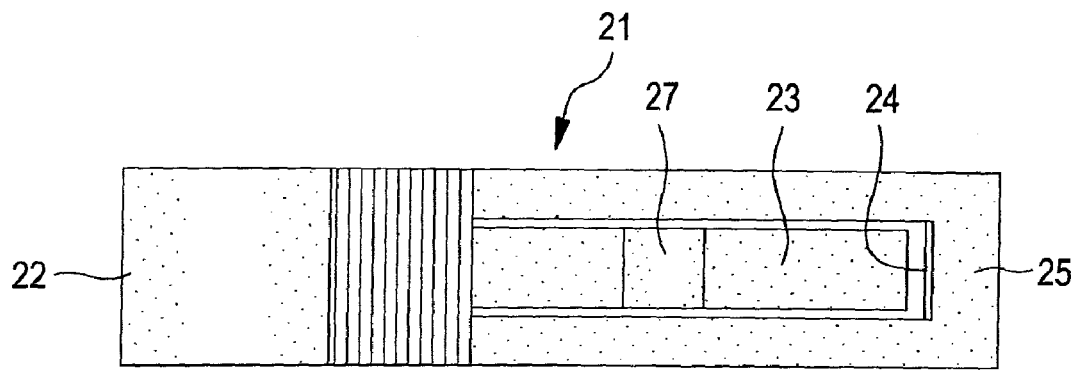
FIG. 3 is a top plan view of the clip.
Figure 4:
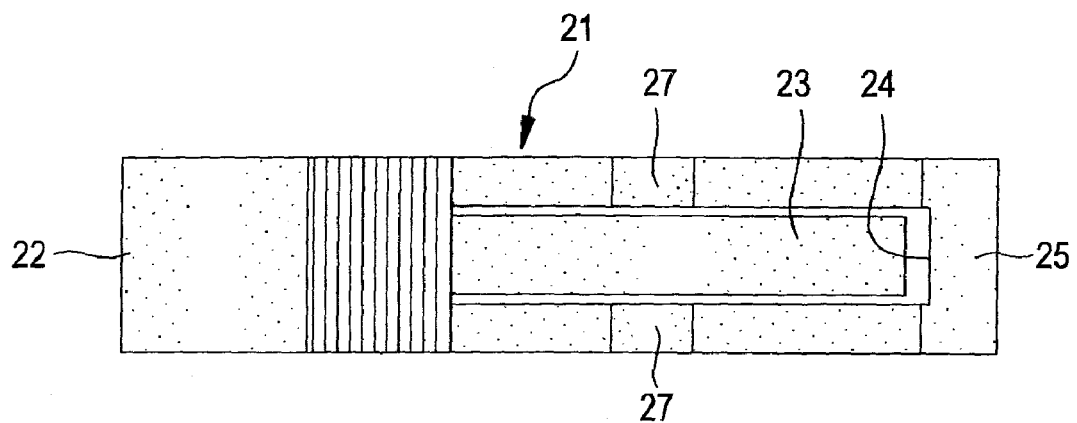
FIG. 4 is a bottom view of the clip.
Figure 5:
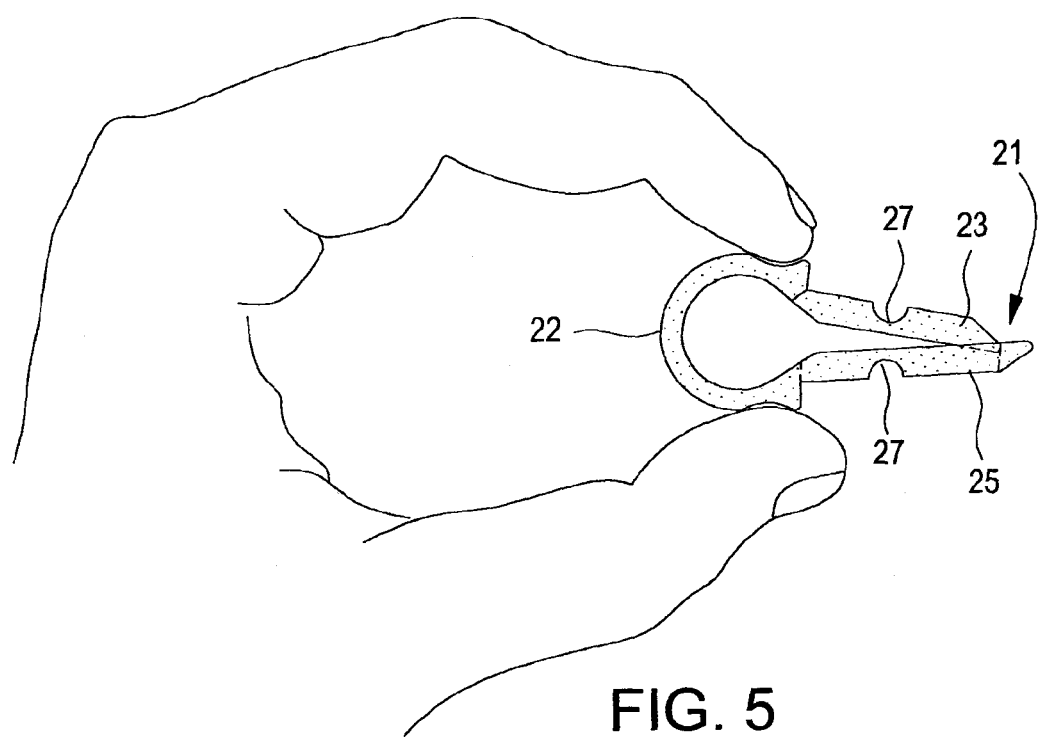
FIG. 5 is an illustrative view of the clip prior to compression.
Figure 6:
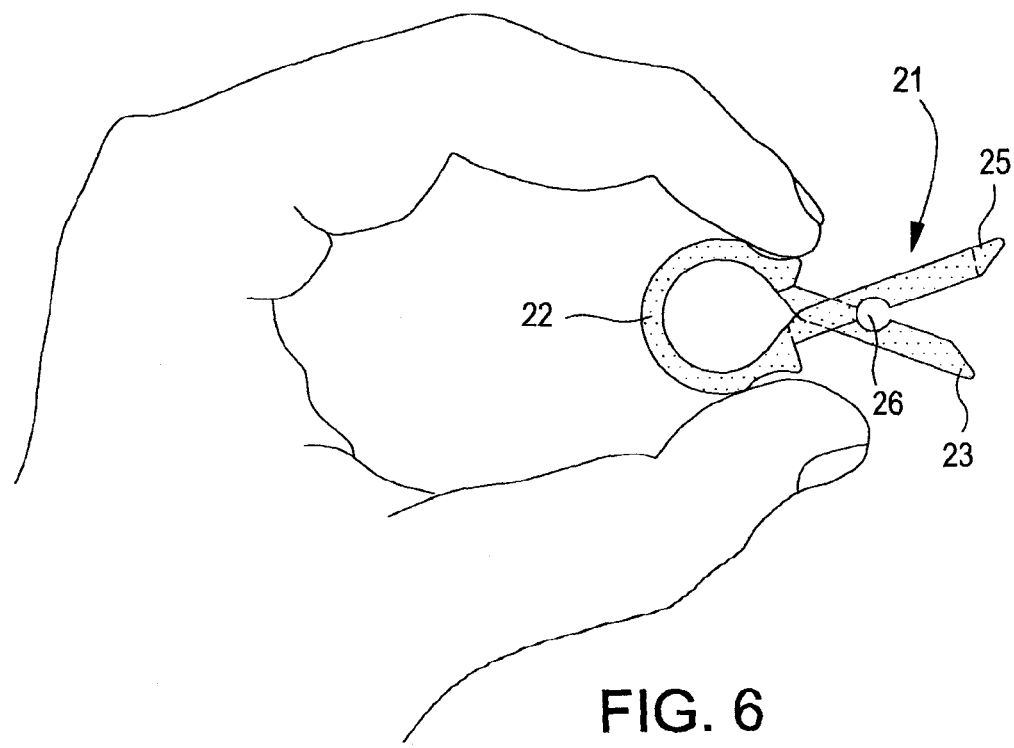
FIG. 6 is an illustrative view of the clip after compression.
Figure 7:
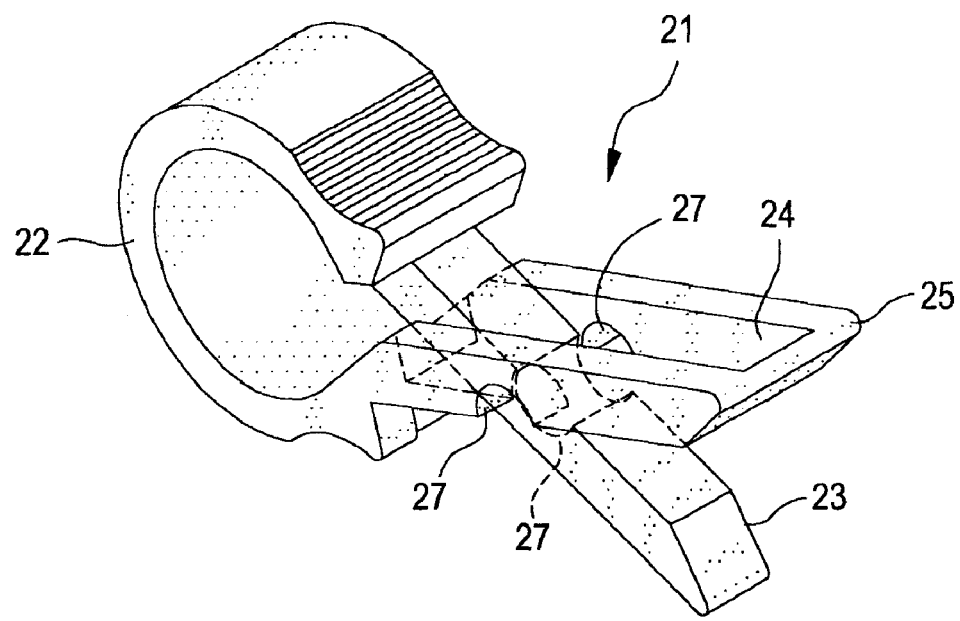
FIG. 7 is a perspective view of the clip after compression.
Figure 8:
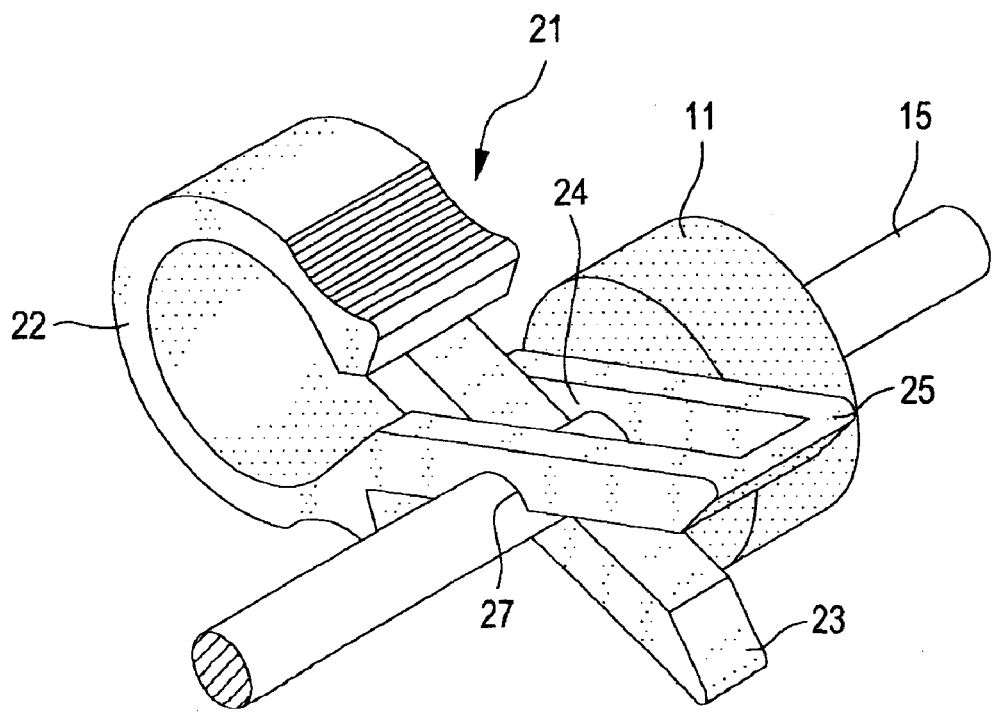
FIG. 8 is a perspective view of the clip secured to a pin adjacent a sponge.

When the clip 21 is compressed, the legs of the clip 21 will cross (FIGS. 6-7) and when released will attach to the full-range of external fixation pins and wires (FIG. 8). The legs of the clip 21 are biased to uncross (FIGS. 1-2 and 5) so that the clip 21 will grip the pin 15 tightly when the clip 21 is decompressed (FIG. 8). This reverse action of the clip 21, opening when compressed and closing when released, is a self-closing and self-holding clip that can be applied and removed with one hand. While other clips may be used in the present invention, the preferred clip is a reverse action clip preferably comprising unitary molded plastic because it is a single-piece structure that is inexpensive to manufacture, not requiring assembly or a secondary manufacturing operation, and it will clamp securely to the full range of pin and wire diameters.

The clip (FIGS. 1-8) is preferably a pinch-type clip 21 that opens by compressing the C-shaped head 22 of the clip 21 so that the short arm 23 passes through an opening 24 formed in the long arm 25, thereby allowing the pin to be received within a channel 26 formed by opposing semicircular slots 27 formed in the arms 23, 25. The clip face that abuts the sponge 11 has openings adequate to allow access for application of antiseptic, antibiotic, or other medications as prescribed by the patient's physician. A unit of the system will preferably comprise a medical grade clip, preferably made of a plastic such as virgin homopolymer polypropylene, and a cylindrical or hemispherical sponge, preferably made of absorbent hydroxylated polyvinyl acetal or some other absorbable medical grade sponge. Although the preferred clip is comprised of a unitary molded plastic, other materials such as metal or wire could be used to obtain the same design and function. Further, the clip could be used in other applications.

While the invention has been shown and described in some detail with reference to specific exemplary embodiments, there is no intention that the invention be limited to such detail. On the contrary, the invention is intended to include any alternative or equivalent embodiments that fall within the spirit and scope of the invention as described and claimed herein.

The invention claimed is:

1. A method for securing a sponge to a pin adjacent a wound in a pin site wound protection system, comprising the steps of:
   a. applying a hemispherical sponge to said pin adjacent the wound, wherein said sponge has a spiral cut therein that extends from an exterior surface of said sponge to a central axial opening through said sponge and said sponge is twisted onto said pin such that said pin travels through said spiral cut until said pin is within a said central axial opening through said sponge; and
   b. applying a spring-loaded clip to said pin adjacent said sponge to secure said sponge adjacent the wound.

2. A method according to claim 1, wherein said clip comprises a unitary member having a C-shaped head, a short arm having a slot formed in an outwardly facing external surface thereof, and a long arm having at least one slot formed in an outwardly facing external surface thereof and a longitudinal opening through said long arm, wherein said head can be compressed such that a terminal end of said short arm distal of said slot in said short arm passes completely through said opening in said long arm, thereby allowing said pin to be received within a channel formed by said slots in said short and long arms.

3. A method for securing a sponge to a pin adjacent a pin site wound, comprising the steps of:
   a. applying a hemispherical sponge to said pin adjacent the wound, wherein said sponge has a spiral cut therein that extends from an exterior surface of said sponge to a central axial opening through said sponge and said sponge is twisted onto said pin such that said pin travels through said spiral cut until said pin is within a said central axial opening through said sponge; and
   b. applying a securing member to said pin adjacent said sponge to secure said sponge adjacent the wound.

4. A method according to claim 3, wherein said securing member comprises a unitary member having a C-shaped head, a short arm having a slot formed in an outwardly facing external surface thereof, and a long arm having at least one slot formed in an outwardly facing external surface thereof and a longitudinal opening through said long arm, wherein said head can be compressed such that a terminal end of said short arm distal of said slot in said short arm passes completely through said opening in said long arm, thereby allowing said pin to be received within a channel formed by said slots in said short and long arms.

5. A method for securing a sponge to a pin adjacent a pin site wound, comprising the steps of:
   a. applying a sponge to said pin adjacent the wound; and
   b. applying a spring-loaded clip to said pin adjacent said sponge to secure said sponge adjacent the wound, wherein said clip comprises a unitary member having a C-shaped head, a linear short arm having a slot formed in an outwardly facing external surface thereof, and a linear long arm having at least one slot formed in an outwardly facing external surface thereof and a longitudinal opening through said long arm, wherein said head can be compressed such that a gist-at terminal end of said short arm distal of said slot in said short arm passes completely through said opening in said long arm, thereby allowing said pin to be received within a channel formed by said slots in said short and long arms.

6. A method according to claim 5, wherein said sponge has a spiral cut therein that extends from an exterior surface of said sponge to a central axial opening through said sponge and said sponge is twisted onto said pin such that said pin travels through said spiral cut until said pin is within said central axial opening through said sponge.

7. A method according to claim 5, wherein said sponge is hemispherical.

\* \* \* \* \*